United States Patent [19]
Chandra

[11] Patent Number: 5,556,644
[45] Date of Patent: Sep. 17, 1996

[54] NUTRITIONAL SUPPLEMENT FOR THE ELDERLY

[75] Inventor: Ranjit K. Chandra, St. Johns, Canada

[73] Assignee: Chandra Consultants, St. Johns, Canada

[21] Appl. No.: 383,490

[22] Filed: Feb. 3, 1995

Related U.S. Application Data

[62] Division of Ser. No. 971,622, Nov. 5, 1992, abandoned.

[51] Int. Cl.$^6$ .............. A61K 33/34; A61K 33/32; A61K 33/26; A61K 33/14
[52] U.S. Cl. .............. 424/630; 424/643; 424/646; 424/678; 424/681; 514/169; 514/276; 514/355; 514/356; 514/458; 514/474; 514/725
[58] Field of Search .................. 424/630, 643, 424/646, 678, 681; 514/169, 276, 355, 356, 458, 474, 725

[56] References Cited

U.S. PATENT DOCUMENTS

| | | | |
|---|---|---|---|
| 2,841,528 | 7/1958 | Myhre | 167/82 |
| 3,243,347 | 3/1966 | Kracauer | 167/81 |
| 4,216,236 | 8/1980 | Mueller et al. | 462/72 |
| 4,629,625 | 12/1986 | Gaull | 424/145 |
| 4,710,387 | 12/1987 | Uiterwaal et al. | 426/72 |
| 4,804,535 | 2/1989 | Kesselman et al. | 424/141 |
| 4,871,550 | 10/1989 | Millman | 424/601 |
| 5,108,674 | 4/1992 | Mulchandani et al. | 426/72 |
| 5,178,878 | 1/1993 | Wehling et al. | 424/466 |

OTHER PUBLICATIONS

R. H. Garrison et al. "The Nutrition Desk Reference" ©1985, pp. 116–124.
1989: "Nutritional Regulation of Immunity and Risk of Infection in Old Age": Heath Clarke Lecture–Univ. of London
Geritol Extend label–package: Smith Kline Beecham Consumer Brands (1992).
Centrum Silver label–package: Lederle Laboratories (1992).

*Primary Examiner*—Raymond Henley, III
*Attorney, Agent, or Firm*—Myers, Liniak & Berenato

[57] ABSTRACT

A multinutrient nutritional supplement is provided that is designed to be most effective in increasing the immunity and decreasing the instances and severity of infection particularly among older persons.

2 Claims, 1 Drawing Sheet

NUTRITIONAL SUPPLEMENT FOR THE ELDERLY

This is a division of application Ser. No. 07/971,622 filed Nov. 5, 1992 now abandoned.

BACKGROUND OF THE INVENTION

The present invention relates to a multinutrient supplement. More particularly, the present invention relates to a multivitamin multimineral supplement intended to be particularly useful for those adult humans over 65 years of age in improving immune system response and reducing the frequency of infection and in particular, respiratory infection.

The proportion and absolute number of individuals above the age of 65 years has grown steadily in most countries, particularly in industrialized nations and this trend is likely to continue for at least the next 100 years. At the same time, it is recognized that the elderly are ill much more often than are younger individuals. For this reason, the elderly consume almost 40% of health care resources even though they constitute only 11% of the population today. Thus the state of their health is a matter of great concern not only to the elderly themselves, but also to physicians, sociologists and health administrators.

Although both nutrition and immunology are old disciplines, it has only been about 20 years since the first systematic studies on malnutrition and immunocompetence were conducted. It is now established that nutritional deficiencies are associated with impaired immune responses. Thus, the question no longer is whether malnutrition affects immune responses, but what aspects it affects and to what extent.

Much of the early nutritional work was done on young children in developing countries, but the results of those studies have been shown to be applicable to individuals and populations in industrialized countries and to other age groups, including the elderly. Indeed there are many similarities between young infants and the elderly. Both have less than optimum immune responses, both are at high risk of developing infection, and in both, dietary factors may be important.

The main theories of ageing can be grouped into two broad types. One states that ageing is an orderly, genetically programmed event, which is the consequence of differentiation, growth and maturation. The other attributes ageing to a progressive accumulation of faulty molecules resulting in cell dysfunction and death; this may be a stochastic event resulting from random synthetic errors or a progressive damage to molecules due to their inherent instability or to environmental influences. If, for a moment, we discard the preprogrammed event theory, we have to entertain the possibility that ageing is associated with a progressive accumulation of faulty molecules and cells, which then results in a decline of physiological function, vulnerability to disease, illness, and death. Such a process can be hastened by adverse environmental factors such as nutritional deficiencies.

Ageing is generally associated with impaired immune responses. The pattern of illness observed in the elderly suggests that immune responses decline in old age. Indeed this has been shown both in man and laboratory animals. This may partly explain the frequent occurrence of infections in old age. Because of the close contact of the immune system with other systems in the body, any changes in immunocompetence may be expected to influence other organ functions as well. As immunological vigour declines, the incidence of infections, cancer, immune complex disease, autoimmune disorders, and amyloidosis increases. Infection, particularly, respiratory infection, is a major cause of illness and the fourth most frequent cause of death among the elderly. However, at least 25% of old individuals have vigorous immune responses at levels observed in young adults. Cellular and molecular manipulation to prevent or slow the decline of immune functions may be expected to delay the onset or decrease the severity of pathology associated with ageing.

It is now well established that nutrition is a critical determinant of immunocompetence. Protein-energy malnutrition and deficiencies of various nutrients impair several immune responses, particularly cell-mediated immunity. Considerable data indicate that nutritional problems are common in old age. Furthermore, the simultaneous assessment of nutritional status, immune responses and subsequent correlation analysis have suggested that impaired immunity in the elderly may be due in part to the associated nutritional deficiencies. There are limited observations to suggest that supplementation with selected nutrients may improve certain aspects of the immune system.

The well-documented effects of various nutrients in the maintenance of optimum immunity has led to limited studies of supplementation with a single nutrient or a group of nutrients. The administration of moderate amounts of zinc to subjects over 70 years of age was associated with improved delayed cutaneous hypersensitivity. In another study, such a supplement increased the number of circulating T cells, delayed cutaneous hypersensitivity and serum IgG antibody response to tetanus toxoid. The addition of zinc in vitro corrected impaired natural killer cell activity. Vitamin C supplement enhanced lymphocyte proliferation in vitro and skin reactivity to tuberculin in vivo. However, the use of megadoses of any nutrient is unwise. Large doses of zinc impair cell-mediated immune responses and neutrophil function and similar adverse effects have been shown for large doses of selenium, vitamin E and vitamin A.

The studies done to date on this subject, however, have suffered from a number of problems including use of an insufficient number of subjects, employed large pharmacologic doses of single or only a few nutrients and the duration of supplementation and follow up was limited. It has also been shown that the use of a single nutrient in large doses may create secondary alterations in requirements and malabsorption of other nutrients, and in some instances, impair immune responses or be potentially toxic. Similar effects have been shown for certain combinations of nutrients particularly those combinations concerning large amounts of iron. In one report, dietary intakes of vitamins E and D negatively systematically.

Known nutritional supplements fall into these basic categories; (1) single nutrient supplements;(2) multinutrient supplements; and (3) multinutrient supplements that are designed for individuals over 50 years of age. The problems associated with single nutrient supplements are first that they, by their definitions, contain only a single nutrient and as discussed above, large doses may have the negative effect of incurring secondary effects or of being potentially toxic. Standard multinutrient supplements such as, for example those sold under the trademarks Nature's Bounty 1, Vita Lea and Centrum as set forth in U.S. Pat. No. 4,629,625 to Gaull, generally have megadoses of component nutrients, lack certain nutrients altogether or have dosages of nutrients based upon the U.S. RDA which establishes guidelines and dietary recommendations for an age group that is completely different than the elderly. Those multinutrient supplements that have targeted individuals over 50 years of age, such as those sold under the trademarks Geritol Extend and Centrum Silver have either lacked some important nutrients, contain unduly high doses of preformed vitamin A which could prove detrimental and/or contain levels of beta-carotene and doses of preformed vitamin A which could prove detrimental and/or contain levels of beta-carotene and vitamin E that are too low.

It is apparent from the foregoing, given the known correlation between proper nutrition and immune responses particularly in the case of elderly persons with impaired immune responses, that the need exists for a multinutrient dietary supplement specifically formulated for the needs of older persons that is effective in improving their immune responses and reducing their frequency of infection, in particular respiratory infection.

SUMMARY OF THE INVENTION

Accordingly, it is an object of the present invention to provide a multinutrient supplement specifically designed to meet the nutritional needs of older persons.

It is another object of the present invention to provide a multinutrient supplement that improves immune system response and is effective in the prevention of infection and particularly respiratory infection in elderly persons.

It is yet another object of the present invention to provide an improved multinutrient supplement for the elderly that promotes higher numbers of selected T cell subsets and natural killer cells, enhanced lymphocyte proliferation, enhanced proliferation response to mitogen, increased interleukin-2 production and higher antibody response and natural killer cell activity.

These and other objects of the present invention are satisfied by a multinutrient supplement comprising about 340 to 460 RE of vitamin A; 13.6 to 18.4 mg of beta-carotene; 1.9 to 2.5 mg of Thiamin (B1); 1.3 to 1.7 mg of Riboflavin (B2); 13.6 to 18.4 mg of Niacin; 2.55 to 3.45 mg of vitamin B6; 340 to 460 ug of Folate; 3.4 to 4.6 ug of vitamin B12; 68 to 92 mg of vitamin C; 3.4 to 4.6 ug of vitamin D; 37.4 to 50.6 mg of vitamin E; 13.6 to 18.4 mg of Iron; 13.9 to 16.1 mg of Zinc; 1.2 to 1.6 mg of Copper; 17 to 23 ug of Selenium; and 170 to 230 ug of Iodine.

Further objects, features and advantages of the present invention will become apparent from the detailed description which follows, considered together with the attached claims.

DETAILED DESCRIPTION OF THE INVENTION

Figure 1:
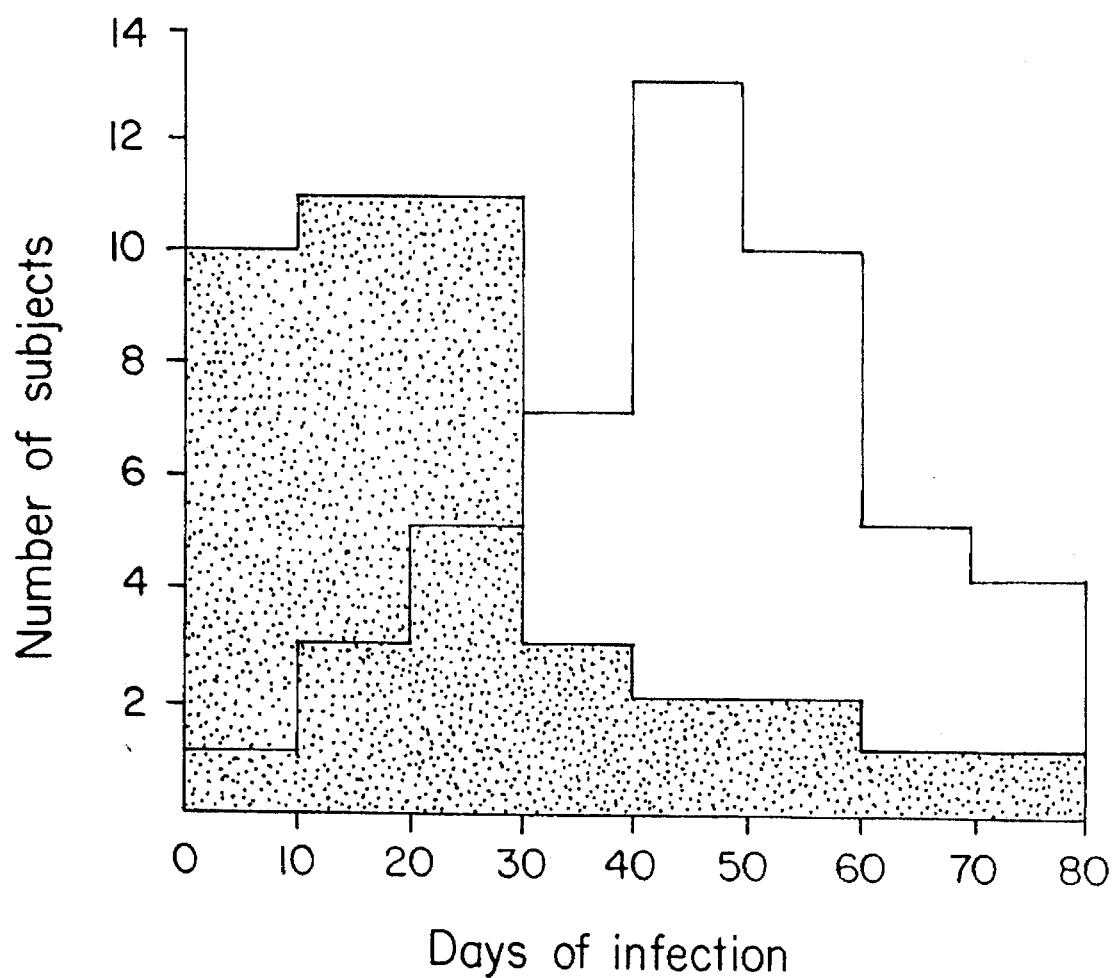
FIG. 1 is a graphical representation of the distribution of infection related morbidity for a study group of individuals that took either a multinutrient supplement according to the present invention or a placebo.

As described above, research has indicated that nutrition is a critical determinant of immunocompetence. Protein-energy malnutrition and deficiencies of various nutrients impair several immune responses, particularly cell mediated immunity. Considerable data indicate that nutritional problems are common in old age. There are limited observations to suggest that supplementation with selected nutrients may improve certain aspects of the immune system.

Given the problems of single nutrient large dose supplements, such as the potential creation of secondary alterations in requirements and malabsorption of other nutrients, the approach of the present invention is to provide a multinutrient supplement. The selection of the number, type and amount of nutrients in the present invention has been carefully optimized to provide the desired result of improving immune response and thereby decreasing the number and severity of infections in an elderly population as a result of an increased number of selected T cell subsets and natural killer cells, enhanced proliferation response to mitogen, enhanced lymphocyte proliferation, increased interleukin-2 production, and higher antibody response and natural killer cell activities.

The optimization of the present invention involved selection of the proper number and type of nutrients to insure that the multinutrient supplement would not be under or over inclusive to achieve the desired effect. Likewise, the amount of particular nutrients present was optimized in view of not only the quantity of each element that would bring about the desired result, but also in view of those elements (such as iron for instance) that can create secondary alterations in requirements and malabsorption of other nutrients which could potentially impair immune responses. As a result of this optimization, the specific ingredients and composition of the present invention found to be most beneficial is set forth in Table I.

TABLE I

| GENERAL COMPOSITION | |
|---|---|
| NUTRIENT | PREFERRED RANGE |
| Vitamin A | 340–460 RE |
| Beta-carotene | 13.6–18.4 mg |
| Thiamin (B1) | 1.9–2.5 mg |
| Riboflavin (B2) | 1.3–1.7 mg |
| Niacin | 13.6–18.4 mg |
| Vitamin B6 | 2.55–3.45 mg |
| Folate | 340–460 ug |
| Vitamin B12 | 3.4–4.6 ug |
| Vitamin C | 68–92 mg |
| Vitamin D | 3.4–4.6 ug |
| Vitamin E | 37.4–50.6 mg |
| Iron | 13.6–18.4 mg |
| Zinc | 13.9–16.1 mg |
| Copper | 1.2–1.6 mg |
| Selenium | 17–23 ug |
| Iodine | 170–230 ug |
| Calcium | 170–230 mg |
| Magnesium | 85–115 mg |

It should be noted that for reasons to be discussed in more detail later, it is believed that the nutrients calcium and magnesium did not provide any particular immunologic health benefit in the context of the desired result of the present invention. Also, although all of the other nutrients set forth in Table I are deemed to be important in achieving the desired result of the present invention, it is believed that the most important elements of the multinutrient supplement according to the present invention are: vitamin A, beta-carotene, vitamin B6, vitamin E, iron and zinc with the next most important elements being: folate, vitamin C and copper.

From the preferred ranges set forth in Table I, a particularly preferred composition of a multinutrient supplement according to the present invention was arrived, selected and the results tested. A detailed description of this embodiment of the present invention and its beneficial facts follows.

EXAMPLE 1

A most preferred embodiment multinutrient supplement consisted of the following:

TABLE II

| Nutrient | Amount Present |
| --- | --- |
| Vitamin A | 400 RE |
| Beta-carotene | 16 mg |
| Thiamin (B1) | 2.2 mg |
| Riboflavin (B2) | 1.5 mg |
| Niacin | 16 mg |
| Vitamin B6 | 3 mg |
| Folate | 400 ug |
| Vitamin B12 | 4 ug |
| Vitamin C | 80 mg |
| Vitamin D | 4 ug |
| Vitamin E | 44 mg |
| Iron | 16 mg |
| Zinc | 14 mg |
| Copper | 1.4 mg |
| Selenium | 20 ug |
| Iodine | 200 ug |
| Calcium | 200 mg |
| Magnesium | 100 mg |

Pure nutrient substances in the proportions set forth were dry blended using a powder mill unit until they mixed to form a resultant multinutrient powder. The blending was effected under conditions which yielded particle sizes of less than 50 microns. Resulting powder of a sufficient amount was then packed into opaque nonallergenic capsule shells having an outer dimension length of 18 mm and a 6 mm diameter such as those made for example by the Parke Davis Company to yield the amounts indicated above designed for use as a nutritional supplement once a day. A placebo was similarly prepared that contained only 200 mg of calcium and 100 mg of magnesium per supplement and no additional nutrients. Since this placebo was used as the control in a study to determine the effect of the most preferred embodiment on the immune responses of elderly subjects taking that nutritional supplement, no immunologic health benefit is being claimed for these two elements.

In an attempt to study the effectiveness of the present invention, senior citizens identified from the St. John's, Newfoundland city census were contacted and those who were apparently healthy and independently living were approached to take part in a trial of the invention. Ninety-six men and women above 65 years of age volunteered for the double-blind placebo-controlled trial. All subjects were of English or Irish ancestry and of middle class socioeconomic status. All individuals approached enrolled in the study and informed consent was obtained. None of the subjects had any known chronic or serious illness nor were they taking medications that might have interfered with nutritional status or immunocompetence. The subjects were randomly assigned to receive either the placebo or the nutrient supplement based on four blocks of 24 random numbers. Participants were unaware of the group to which they had been allocated.

The daily oral supplement contained the micronutrients set forth previously in Table II. The amounts of various nutrients were somewhat similar to the Recommended Nutrient Intakes in Canada and the Recommended Dietary Allowances in the U.S.A. with the exception of beta-carotene and vitamin E which were provided at about 4 times the upper quartile of usual intakes and, as previously discussed, placebo contained calcium 200 mg and magnesium 100 mg. The multinutrient supplement and the placebo were identical and were prepared specifically for this study. Neither the subjects nor the observers and laboratory personnel were aware of the nature of the supplement given. Study participants were advised to continue their normal activity and to report any unusual symptoms or change in appetite or weight.

Compliance was verified by interview at fortnightly visits and counting left over medication. Physiological steps were taken to insure that the effects of dietary supplementation according to the present invention would be properly detected. Table III (see attached) shows Reference Standards for Blood Nutrient Values assay procedures and 95 percent confidence intervals derived as mean±standard deviation from evaluation of fasting blood samples of healthy men and women, 66–88 years of age, living in Newfoundland. Each subject had been followed for 1–3 years to ensure that they had remained healthy. All individuals were Caucasians and in the upper middle to high socioeconomic strata. The number of subjects on which the confidence intervals are based was between 38 and 141 for various tests. The distributions of values were approximately normal.

Subjects in the randomized trial whose blood nutrient values fell below the 95 percent confidence limits of these "normal" reference standards were defined as deficient.

Complete hemogram and blood counts were obtained. Peripheral blood mononuclear cells were separated from heparinized blood by density gradient centrifugation. Cells were washed and used for enumeration of subsets using commercial monoclonal antibodies, for production of interleukin-2, and for natural killer cell activity by previously described and established techniques. Subjects were tested at the onset of the study and again at the end of 12 months of administration of placebo or supplement. Influenza vaccine was given 4 weeks prior to the end of the study period and antibody level estimated. For all laboratory tests, the average of three estimations was used in analysis.

Subjects were asked to contact the principal investigator or his clinical delegate in the event of any illness. The diagnosis of infection was based on clinical features and a battery of appropriate laboratory tests as indicated; blood counts, X-ray of the chest and sinuses, bacterial and fungal cultures of the sputum, urine and blood, C-reactive protein, endotoxin and ESR. Those diagnosed to have infection were treated appropriately with antimicrobial agents and supportive measures. Additional illness data was collected from personal interviews conducted by a research assistant every two weeks throughout the study period. Information obtained in these sessions was supported by reports of respective family physicians and hospital out-patient clinics.

The number of individuals defined as deficient for a given nutrient at 0 and 12 months was compared for each group by the Chi square or Fisher's exact probability test. The mean change in immune responses per individual was compared in the two groups using an unpaired t-test. Results of immune responses were correlated with blood nutrient levels by Pearson's correlation coefficient. Morbidity and antibiotic use in the placebo and supplemented groups was compared by the unpaired Wilcoxon signed-sum test. Statistical tests were conducted on appropriately transformed data when the observed values were not distributed normally.

RESULTS AND DISCUSSION

The two groups were matched in age and gender ratio in Table IV (see attached). Seven subjects in the placebo group and three in the supplement group were dropped from the final analyses. Two individuals in the placebo group died during the trial, one of cerebrovascular accident and another of lung cancer. Five subjects in the placebo group and three in the supplement group withdrew from the study because of personal reasons.

The frequency of nutrient deficiencies at the onset of the study was comparable in the two groups. At the inceptions of the study (0 month), the prevalence of deficiency was not different between the two groups for any of the nutrients tested. In the placebo group, there was no significant change in the prevalence of deficiencies over the 12-month study period. At the end of the 12 month trial, however, there was a statistically significant reduction in the prevalence of deficiencies of vitamin A, beta-carotene, vitamin B6, vitamin C, iron and zinc in the supplemented group shown in Table IV.

At the end of the trial period, there was no change in the absolute number of neutrophils or lymphocytes. However, there was a statistically significant improvement in several immunological responses, including the number of T cells, CD4+helper cells, CD3+/CD25+IL-2 receptor bearing cells, natural killer cells, lymphocyte response to phytohemagglutinin, production of interleukin-2, IL-2 receptor release, natural killer cell activity and antibody response to influenza vaccine as shown in Table V.

The predominant beneficial effect on cell-mediated immune responses in the elderly is similar to that observed in younger subjects. The improvement in immunological responses was greater in those individuals in the supplemented group who had shown one or more nutrient deficiencies at entry into the study. There was no significant relationship between weight-for-height or mid-arm circumferece and any of the immunological tests in either of the two groups. However, there was a significant correlation between serum ferritin and natural killer cell activity (r=0.61), serum zinc and interleukin-2 production (r=0.69), serum zinc and natural killer cell activity (r=0.48), vitamin B6 and lymphocyte response to mitogen (r=0.38), and beta-carotene and interleukin-2 production (r=0.43).

Furthermore, there was a marked reduction in infection-related illness in the supplemented group (23±5 days per year) compared with the placebo group (48±7 days per year). This difference is statistically highly significant and was the result of a general reduction in infection, rather than a selective reduction affecting only individuals with prolonged illness as shown in FIG. 1. The number of days for which antibiotics were prescribed was also different in the two groups. The results are summarized below in Table VI.

TABLE VI

Morbidity and use of antibiotics

| Group | Morbidity (days/year) | Antibiotic use (days/year) |
|---|---|---|
| Placebo | 48 ± 7 | 32 ± 5 |
| Supplement | 23 ± 5 | 18 ± 4 |
| P | 0.0002 | 0.004 |

Data are shown as mean ± standard deviation

This study confirms the frequent prevalence of micronutrient deficiencies in apparently healthy elderly individuals. The age-associated reduction in immune responses was also demonstrated. Supplementation with modest physiological amounts of essential vitamins and trace elements resulted in a significant improvement in several parameters of immunocompetence. It is important to note that megadose supplements were not used. Indeed our previous experience indicates that very large doses of many micronutrients may impair immunity. For every micronutrient there appears to be an upper and lower threshold for optimal immune function.

The results of this study substantiate the concept that nutritional status is an important determinant of immunocompetence in old age and that an optimal intake of micronutrients results in enhanced immune responses in the elderly. In summary, those who received the supplement had higher numbers of selected T cell subsets and natural killer cells, enhanced proliferation response to mitogen, increased interleukin-2 production, and higher antibody response and natural killer cell activity. The supplemented group experienced fewer days of illness due to infections (23±5 days per year) compared with morbidity in the placebo group (48±7 days per year). It is concluded that supplementation with a modest physiological amount of micronutrients improves immunity and decreases the risk of infection in old age.

In a related study, dosages of various components of the multinutrient supplement according to the present invention were varied to determine whether an appropriate optimum dosage of nutrients had been arrived as measured by resultant immune responses. The expressed results in terms of percentages measured against the previously disclosed and the most preferred embodiment of the invention are summarized in Table VII as follows:

TABLE VII

Dose Responses for Vitamins and Trace Elements

| Nutrient | NK cell activity | T cell response | IL-2 | Morbidity |
|---|---|---|---|---|
| Vitamin A (RE) | | | | |
| 200 | 78 | 65 | 61 | 160 |
| 800 | 83 | 101 | 88 | — |
| 3200 | 64 | 68 | 56 | 140 |
| Beta-carotene (mg) | | | | |
| 4 | 70 | 82 | 65 | 88 |
| 64 | 106 | 92 | 98 | 104 |
| Vitamin B6 (mg) | | | | |
| 1 | 82 | 62 | 53 | — |
| 6 | 102 | 96 | 95 | — |
| Vitamin C (mg) | | | | |
| 20 | 64 | 70 | 73 | 137 |
| 200 | 92 | 103 | 110 | 97 |
| 2000 | 81 | 72 | 89 | 108 |
| Vitamin D (mg) | | | | |
| 2 | 72 | 78 | 84 | 120 |
| 10 | 98 | 92 | 106 | 102 |
| 50 | 92 | 90 | 98 | 96 |
| Vitamin E (mg) | | | | |
| 4 | 68 | 70 | 69 | 124 |
| 800 | 98 | 101 | 108 | 96 |
| 1600 | 81 | 76 | 72 | 116 |
| Iron (mg) | | | | |
| 2 | 56 | 67 | 79 | 118 |
| 32 | 90 | 92 | 101 | 124 |
| Zinc (mg) | | | | |
| 4 | 68 | 71 | 72 | 128 |
| 25 | 87 | 80 | 91 | 121 |
| 100 | 66 | 64 | 58 | 138 |
| Selenium (ug) | | | | |
| 80 | 81 | 72 | 69 | — |
| 160 | 61 | 53 | 59 | — |

[All results are expressed as % of most preferred embodiment]

Although the present invention is directed primarily to those persons over 65 years of age, it should be understood that the beneficial results arrived at through use of the multinutrient supplement in accordance with the present invention would render the same or similar beneficial results in many populations of individuals that fall under 65 years of age as well. In particular, those individuals between 50 and 65 years of age are therefore contemplated as being within the scope of the terms "elderly" and "older persons" when used in the context of the present invention. Additionally it should also be understood that the benefits similar to those described above may still occur in multinutrient compositions that may not contain one of the nutrients of the present invention that have previously been described as having secondary importance.

Although this invention has been described in terms of certain preferred compositions within a stated range, and certain discrete method steps, other embodiments that are apparent to those of ordinary skill in the art are also within the scope of this invention. Accordingly, the scope of the invention is intended to be determined by reference to the appended claims.

I claim:

1. A method of improving the immunological status of elderly persons consisting essentially of the steps of:
    providing to elderly persons individual dosages of a nutritional supplement consisting essentially of:
    about 400 RE of Vitamin A;
    about 16 mg of Beta-carotene;
    about 2.2 mg of Thiamin (B1);
    about 1.5 mg of Riboflavin (B2);
    about 16 mg of Niacin;
    about 3 mg of Vitamin B6;
    about 400 ug of Folate;
    about 4 ug of Vitamin B12;
    about 80 mg of Vitamin C;
    about 4 mg of Vitamin D;
    about 44 mg of vitamin E;
    about 16 mg of Iron;
    about 14 mg of Zinc;
    about 1.4 mg of Copper;
    about 20 ug of Selenium; and
    about 200 ug of Iodine; and
    administering said individual dosages of said nutritional supplement to elderly persons.

2. A method of improving the immunological status of elderly persons consisting essentially of the steps of:
    providing to elderly persons individual dosages of a nutritional supplement consisting essentially of:
    about 400 to 440 RE of vitamin A;
    about 16 to 18 mg of beta-carotene;
    about 2.2 to 2.4 mg of Thiamin (B1);
    about 1.5 to 1.6 mg of Riboflavin (B2);
    about 16 to 16.8 mg of Niacin;
    about 3 to 3.2 mg of vitamin B6;
    about 400 to 450 ug of Folate;
    about 4 to 4.5 ug of vitamin B12;
    about 80 to 90 mg of vitamin C;
    about 4 to 4.5 ug of vitamin D;
    about 44 to 50 mg of vitamin E;
    about 14 to 16 mg of Iron;
    about 14 to 16 mg of Zinc;
    about 1.4 to 1.5 mg of Copper;
    about 20 ug of Selenium; and
    about 200 to 220 ug of Iodine; and
    administering said individual dosages of said nutritional supplement to elderly persons.

* * * * *